(12) United States Patent
Chen et al.

(10) Patent No.: US 12,173,273 B2
(45) Date of Patent: Dec. 24, 2024

(54) LARGE-SCALE MAGNETIC PURIFICATION SYSTEM

(71) Applicant: Nanjing GenScript Biotech Co., Ltd., Jiangsu (CN)

(72) Inventors: Guodong Chen, Nanjing (CN); Zaidong Feng, Nanjing (CN); Ruina He, Nanjing (CN); Hong Qian, Nanjing (CN); Tao Bai, Nanjing (CN)

(73) Assignee: NANJING GENSCRIPT BIOTECH CO., LTD., Jiangsu (CN)

( * ) Notice: Subject to any disclaimer, the term of this patent is extended or adjusted under 35 U.S.C. 154(b) by 897 days.

(21) Appl. No.: 17/288,491

(22) PCT Filed: Oct. 25, 2019

(86) PCT No.: PCT/CN2019/113261
§ 371 (c)(1),
(2) Date: Apr. 23, 2021

(87) PCT Pub. No.: WO2020/083373
PCT Pub. Date: Apr. 30, 2020

(65) Prior Publication Data
US 2021/0388307 A1 Dec. 16, 2021

(30) Foreign Application Priority Data
Oct. 26, 2018 (CN) .......................... 201811260301.2

(51) Int. Cl.
*B03C 1/28* (2006.01)
*B01F 27/11* (2022.01)
(Continued)

(52) U.S. Cl.
CPC ........... *C12M 47/10* (2013.01); *B01F 27/112* (2022.01); *B01F 27/1144* (2022.01);
(Continued)

(58) Field of Classification Search
CPC ........ C12M 47/10; B03K 1/286; B03K 1/288; C07K 1/14; C12N 15/1013; B01F 27/112; B01F 27/1144; B01F 35/22142
See application file for complete search history.

(56) References Cited

U.S. PATENT DOCUMENTS 8,685,322 B2 * 4/2014 Griebel ................. B01F 31/441
422/63
2007/0092403 A1 * 4/2007 Wirbisky ................. C12N 1/06
422/65

FOREIGN PATENT DOCUMENTS

| CN | 101323454 A | 12/2008 | |
| CN | 207091431 U * | 3/2018 | ............. C12M 1/42 |
| JP | 4805319 B2 * | 11/2011 | ................ B01F 7/16 |

OTHER PUBLICATIONS

CN-207091431-U_English (Year: 2018).*
International Search Report with English Translation and Written Opinion for PCT/CN2019/113261 issued Feb. 1, 2020 (9 pages).

* cited by examiner

Primary Examiner — Youngsul Jeong
(74) *Attorney, Agent, or Firm* — Klarquist Sparkman, LLP

(57) ABSTRACT

The present invention relates to a large-scale magnetic purification system, including: a liquid storage apparatus, capable of being connected to a liquid source and a waste liquid barrel through a liquid path system; a stirring system mounted above the liquid storage apparatus, where a stirring paddle of the stirring system is inserted into the liquid storage apparatus for stirring; magnets mounted around the liquid storage apparatus; a magnet actuating mechanism for manipulating the magnets to move away from or close to the liquid storage apparatus; and a control system, connected to the liquid path system, the magnet actuating mechanism, and (Continued)

the stirring system and controlling the liquid path system, the magnet actuating mechanism, and the stirring system.

12 Claims, 3 Drawing Sheets

(51) Int. Cl.
    *B01F 27/112*     (2022.01)
    *B01F 27/1144*     (2022.01)
    *B01F 35/221*     (2022.01)
    *C07K 1/14*     (2006.01)
    *C12M 1/00*     (2006.01)
    *C12N 15/10*     (2006.01)

(52) U.S. Cl.
    CPC ........ *B01F 35/22142* (2022.01); *B03C 1/286* (2013.01); *B03C 1/288* (2013.01); *C07K 1/14* (2013.01); *C12N 15/1013* (2013.01)

LARGE-SCALE MAGNETIC PURIFICATION SYSTEM

CROSS REFERENCE TO RELATED APPLICATIONS

This is the U.S. National Stage of International Application No. PCT/CN2019/113261, filed Oct. 25, 2019, and published in Chinese under PCT Article 21 (2) as WO2020/083373 on Apr. 30, 2020. PCT/CN2019/113261 claims the benefit of priority from Chinese Patent Application No. 201811260301.1, filed on Oct. 26, 2018.

BACKGROUND

Technical Field

The present invention relates to a large-scale magnetic purification system, which is mainly applied to the field of biological purification, for example, large-scale extraction of proteins and nucleic acids.

Related Art

Usually, a magnetic bead purification method uses a purification system to separate magnetic beads through a magnetic field to achieve the objective of separating and purifying substances such as cells, proteins, or nucleic acids. Compared with the commonly used precipitation method, centrifugation method and column membrane method, the magnetic bead purification method has the characteristics of high extraction efficiency, a high separation speed, low equipment requirements, and the like.

Compared with resin purification, the magnetic bead purification method based on magnetic adsorption can quickly and effectively gather target proteins in samples relying on the principle of magnetism in combination with incubation, thereby effectively avoiding the disadvantages such as limitations of resin on sample pretreatments and sample loading methods, and overcoming the restrictions by column packing and flow rate. A purification method based on magnetic separation achieves automation more easily, and can meet a high-throughput purification requirement for rapid, automatic, and multi-channel simultaneous treatment.

Current magnetic bead purification apparatuses available on the market generally have a relatively low throughput and require extensive manual operations to assist in a purification process. In addition, all the operations are open operations currently, and it is difficult to prevent pollution from an external environment or avoid damage to the environment caused by reagent volatilization in the purification process. Although a magnetic frame in the prior art may meet some customer requirements, various defects still exist. For example: (1) the throughput is low, which cannot meet the requirement of large-scale purification; (2) samples need to be transferred into a centrifuge tube or other containers, the process is complex, and the samples may be damaged; (3) to implement automation, an additional apparatus is needed, which requires an additional cost and occupies an additional space; (4) the shape is fixed and cannot flexibly adapt to the appearance of the container.

In addition, all large-scale purification apparatuses on the market adopt a resin purification mode, which requires deep filtration, consumes a large quantity of disposable consumables, and requires multiple employees to work for a long time.

Therefore, there is a need for an improved magnetic purification system that can implement large-scale magnetic bead purification.

SUMMARY

An objective of the present invention is to provide a large-scale magnetic purification system that does not require centrifugation or deep filtration and can directly purify a fermentation broth and save a lot of consumables and equipment for filtration.

During large-scale magnetic bead purification, magnetic beads are directly in free contact with a culture solution, column packing is not required, and there is no defect caused by directional flow purification. In the large-scale magnetic bead purification, all antibodies have the same chance of contact with magnetic beads. However, in resin purification, contact occurs sequentially from front to back, and the contact probability decreases from a front stage to a back stage. Antibodies collected in the front stage are saturated first, and then antibodies collected in the back stage are saturated. Therefore, the amount of antibody aggregation in the front stage is higher than that in the back stage, resulting in antibody inconsistency. The magnetic beads are reused, and all magnetic beads have the uniform damage. Therefore, the amount of the used magnetic beads is easier to control. However, the resin in the front stage is damaged before the resin in the back stage is damaged, resulting in inconsistency.

It takes ¼ of the time required by the resin purification or even shorter for the large-scale magnetic bead purification to purify the same broth volume.

In order to solve the problems of high cost of consumables, a long operation time, and complex procedures in the existing resin purification technology, the large-scale magnetic purification system of the present invention can easily realize high-throughput sample treatment, reduce the investment of consumables, and reduce a purification period.

The present invention reduces the time consumption and high cost of the traditional process, and simplifies a plurality of steps (centrifugation, deep filtration, sterilization filtration, chromatography, and elution) in the traditional process into a new process (incubation and elution), thereby greatly reducing the labor cost and the material cost.

The use of GMP workshop space and site may be reduced.

According to an aspect of the present invention, a large-scale magnetic purification system is provided, including: a liquid storage apparatus, capable of being connected to a liquid source and a waste liquid barrel through a liquid path system; a stirring system mounted above the liquid storage apparatus, where a stirring paddle of the stirring system is inserted into the liquid storage apparatus for stirring; magnets mounted around the liquid storage apparatus; a magnet actuating mechanism for manipulating the magnets to move away from or close to the liquid storage apparatus; and a control system, connected to the liquid path system, the magnet actuating mechanism, and the stirring system and controlling the liquid path system, the magnet actuating mechanism, and the stirring system.

Preferably, vertical magnets movable into the liquid storage apparatus are further provided, and the vertical magnets enter the liquid storage apparatus by moving in a vertical direction.

Preferably, the magnets are horizontal magnets that are movable in a horizontal direction relative to the liquid storage apparatus.

Preferably, the magnets are vertical magnets that are movable in a vertical direction relative to the liquid storage apparatus.

Preferably, the magnets include horizontal magnets and vertical magnets, the horizontal magnets are movable in a horizontal direction relative to the liquid storage apparatus, and the vertical magnets are movable in a vertical direction relative to the liquid storage apparatus.

Preferably, the liquid storage apparatus is a liquid storage tank.

Preferably, a disposable bag is disposed in the liquid storage tank.

Preferably, the stirring paddle is provided with spiral propeller blades and includes two sets of opposite blades mounted on one blade shaft.

Preferably, the magnets are formed by strong magnets to rapidly adsorb magnetic particles.

Preferably, the magnets include the horizontal magnets and the vertical magnets, and the magnet actuating mechanism includes a horizontal magnet actuating mechanism and a vertical magnet actuating mechanism.

Preferably, the vertical magnets are operable by the vertical magnet actuating mechanism to enter or exit the liquid storage apparatus.

Preferably, a rotation speed of the stirring system is automatically controlled by a speed-adjustable motor, to control rotation of blades at different speeds.

Preferably, a pipeline of the liquid path system is made of a non-sticky material for magnetic beads, to reduce loss of the magnetic beads.

According to another aspect of the present invention, a method for purifying a biological sample is provided, including a step of injecting a biological sample containing a target component and magnetic beads capable of binding the target component into a liquid storage apparatus of the large-scale magnetic purification system according to the above descriptions to perform a purification treatment by using the large-scale magnetic purification system.

Preferably, a single injection of the biological sample into the liquid storage apparatus for purification is in a range of 100 mL to 10000 L, preferably 1 L to 1000 L, or more preferably 10 L to 500 L.

BRIEF DESCRIPTION OF THE DRAWINGS

The accompanying drawings schematically show a large-scale magnetic purification system and components according to preferred embodiments of the present invention. The accompanying drawings are merely exemplary and are not necessarily to scale.

DETAILED DESCRIPTION

To describe the technical solutions in the embodiments of the present invention more clearly, specific implementations of the present invention are described below with reference to the accompanying drawings. Obviously, the accompany drawings described in the following are merely some exemplary embodiments of the present invention.

Figure 5:
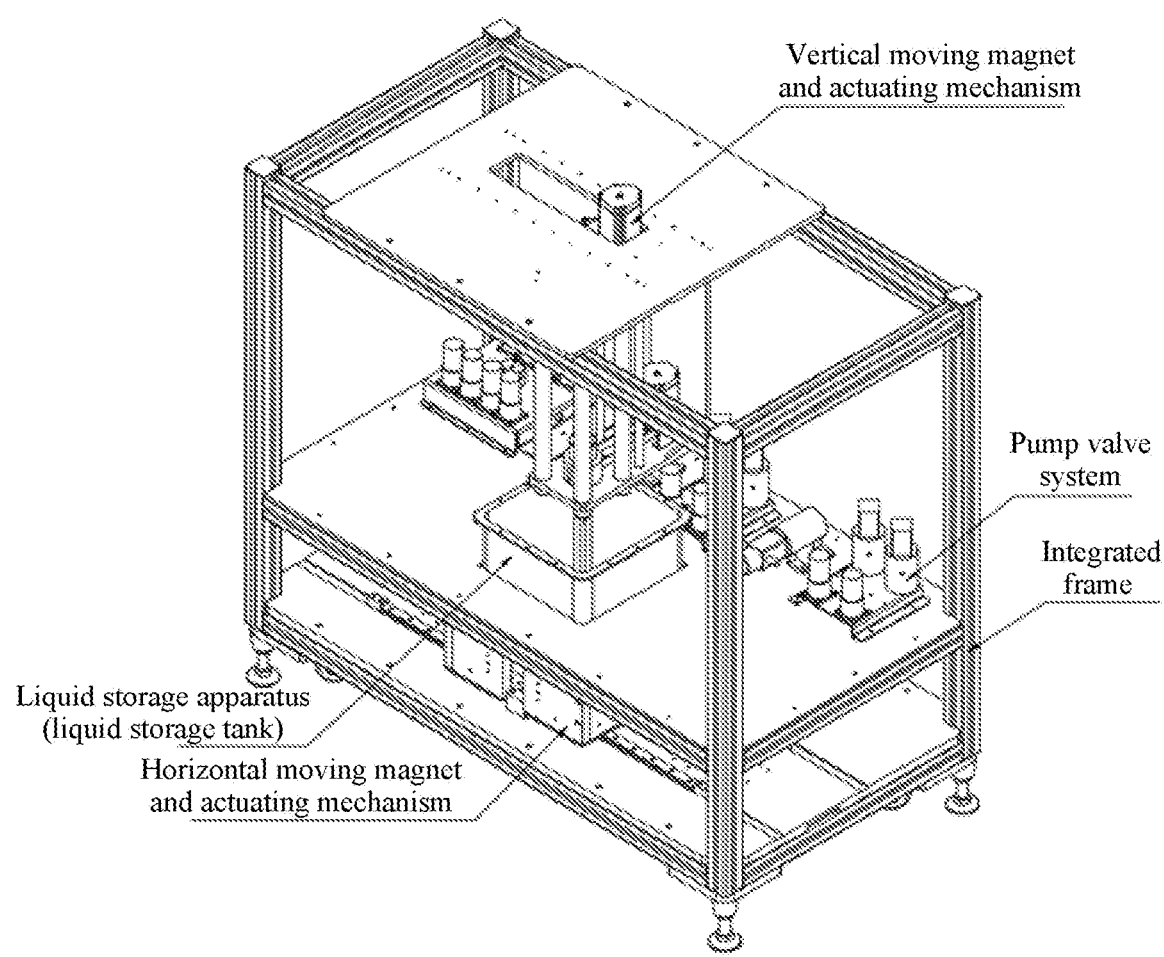
FIG. 5 shows an overall structure of a magnetic purification system according to an exemplary embodiment of the present invention.

According to the present invention, as shown in FIG. 5, a large-scale magnetic purification system is provided, which mainly includes a liquid storage apparatus, a stirring system, magnets, and a magnet actuating mechanism. In the preferred embodiment, the liquid storage apparatus, the stirring system, the magnet, and the magnet actuating mechanism are all mounted on a frame structure. In addition, the large-scale magnetic purification system may further include a pump valve system, to implement supply and discharge of a liquid.

The liquid storage apparatus, for example, a liquid storage tank, is configured to provide a place for magnetic beads to extract proteins or other to-be-extracted substances from a solution. A volume of the liquid storage tank may be several liters to ten thousand liters. Preferably, the volume is greater than or equal to 10 liters. A disposable bag may be put into the liquid storage tank. The disposable bag for storing a liquid may be made of a non-sticky material for magnetic beads, and a spraying device which may spray on the residual solution and magnetic beads stuck on the wall is disposed in the disposable bag. The disposable bag may have a shape that conforms completely to the inner wall of the liquid storage tank.

Figure 2:
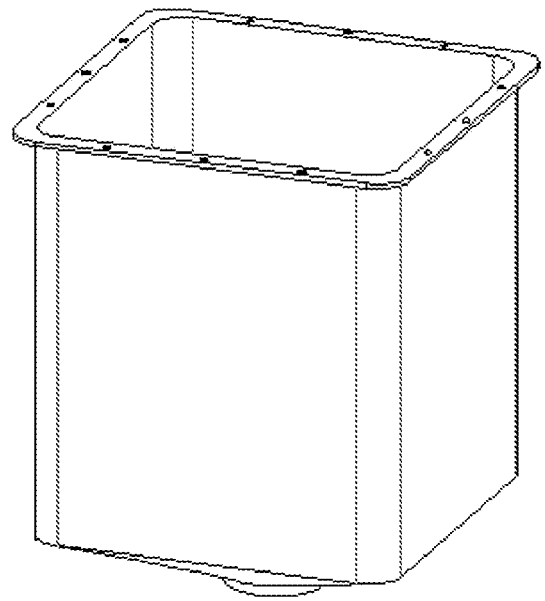
FIG. 2 shows a tank in a magnetic purification system according to an exemplary embodiment of the present invention.

FIG. 2 shows an exemplary liquid storage apparatus, which may be a liquid storage tank, with a capacity of about 10 liters. In other embodiments, the capacity may be larger, for example, 10 liters to 1000 liters. The liquid storage apparatus may be circular or square in shape. For example, square edges are used on the periphery, while transitions between the inner walls of the container are rounded transitions. The container may be made of non-magnetized stainless steel, and the bottom of the container is inclined.

Preferably, the disposable bag for storing the liquid is made of a non-sticky material for magnetic beads, and the shape of the disposable bag is customized according to the shape of the liquid storage apparatus, to ensure to the maximum extent that the magnetic beads are closest to the magnets when being adsorbed. A spraying apparatus which may spray on the residual solution and magnetic beads stuck on the wall is disposed in the disposable bag, to improve a recovery rate of the magnetic beads while making the system cleaner and reducing an infection risk of a purification sample.

Preferably, the container for holding the bag may be provided with square edges at the periphery, so that the magnets perfectly fit the container when adsorbing the magnetic beads. In this way, the most effective distance of the magnets may be used. The four walls of the container use rounded transitions, and the shape of the bag matches that of the container, so that the disposable bag is easily placed into the container without any folding, thereby ensuring the recovery rate of the magnetic beads. The container is made of non-magnetized stainless steel, to ensure that the magnetic beads can be freely mixed in the solution when a magnetic field is removed. The bottom of the container is inclined, which can reduce a final residual volume of the solution, and increase a liquid level in the case of a small volume, so that a magnetic force of the magnets can be fully used during small volume elution.

Figure 3:
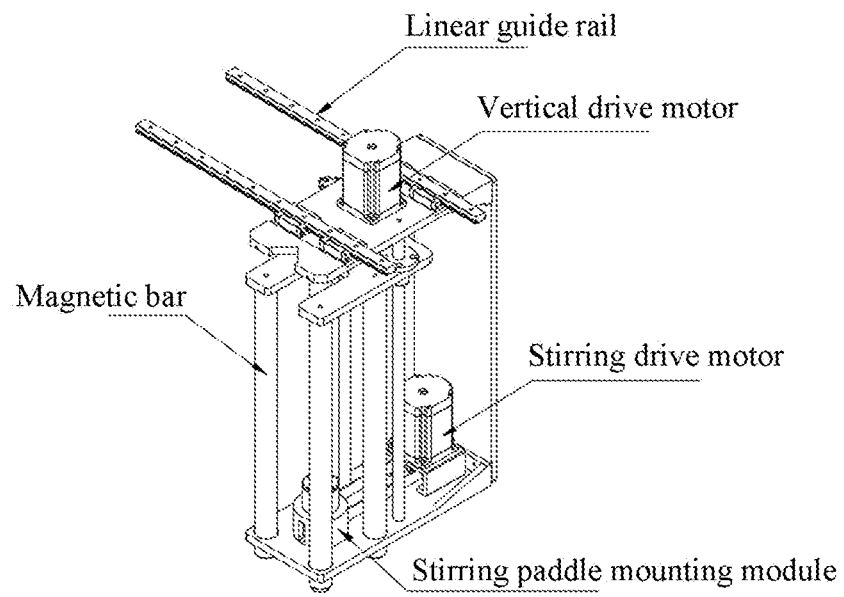
FIG. 3 shows vertical moving magnets, a vertical magnet actuating mechanism, and a stirring system in a magnetic purification system according to an exemplary embodiment of the present invention.

FIG. 3 is a schematic diagram of mounting positions of a stirring paddle mounting module and a stirring drive motor. The figure also shows vertical magnets (for example, magnetic bars), a guide rail, a vertical drive motor, and the like.

The stirring system adopts a speed-adjustable motor to automatically control a rotation speed, and may control the rotation of blades at different speeds, so that the stirring system is used for different conditions respectively. For example, a relatively high rotation speed is used for mixing uniformly, so that the uniform mixing may be performed quickly; a relatively low speed is used for adsorption of the magnetic beads, to achieve a uniform mixing effect while preventing the magnetic beads from being disturbed by the rotation of the blades. Meanwhile, the blades may rotate forward and backward, to better improve the effect of uniform mixing.

The stirring system arranged in the disposable bag may adopt a stainless steel stirring paddle, and the stirring paddle is located in the center of a top surface of the bag. The stirring system adopts the speed-adjustable motor to automatically control the rotation speed, and the blades may rotate forward and backward. A liquid outlet pipe at the bottom is fixed at the bottom of the bag. A liquid inlet enters the bag in a shunting way. The disposable bag may be made of a transparent material.

The size of the blade may be improved to a maximum extent, and the blades are spiral propeller blades. Two sets of opposites blades are mounted on one blade shaft, so that the disturbance of the solution may be increased. The solution is stirred with a rotation speed as low as possible, to improve the effect of liquid mixing to a maximum extent. The reduced blade speed may reduce a shearing force of a blade edge on effective molecules in the solution, thereby preserving maximum activity of the finally collected substance. The liquid outlet pipe at the bottom is fixed in the bottom of the bag, and such a fixing manner may ensure that the magnetic beads are not discharged during liquid discharging, while a maximum amount of waste liquid can be removed. The liquid inlet enters the bag in a shunting way. A solution with more impurities and a larger particle size enters via a wide bore; a clean solution such as a reagent enters via a spraying pipeline, which may rinse the pipeline without blocking the pipeline. The disposable bag is made of the transparent material, so that a user may observe a reaction condition in the solution conveniently during the process.

The stirring system may be located above the liquid storage apparatus. The stirring paddle in the stirring system may extend into the liquid storage apparatus for stirring a mixed liquid uniformly.

A liquid path system is connected to the liquid storage apparatus and a liquid source, for example, a reagent bottle or a reagent pipeline. A pipeline in the liquid path system may be provided with a pump and a valve for sucking and discharging liquid, to supply or discharge the solution to or from the liquid storage apparatus.

Figure 1:
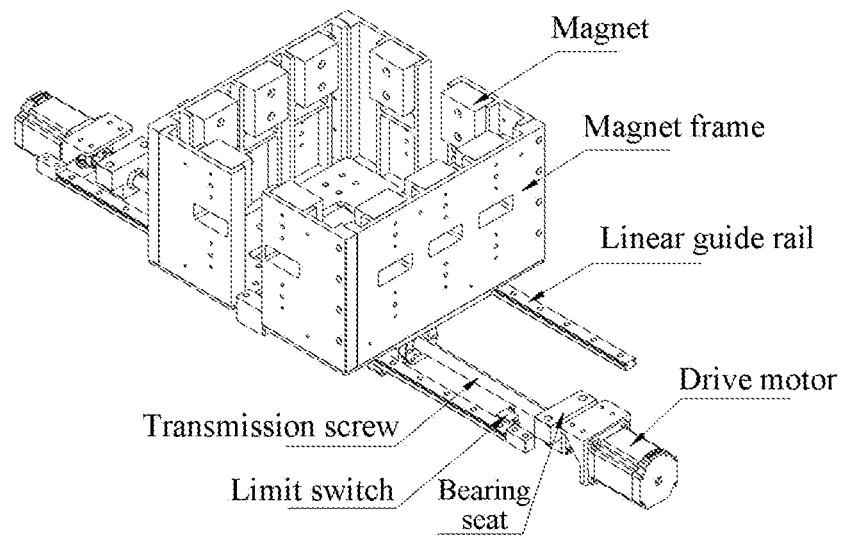
FIG. 1 shows a horizontal moving magnet and a horizontal magnet actuating mechanism of a magnetic purification system according to an exemplary embodiment of the present invention.

FIG. 1 shows exemplary horizontally movable magnets and horizontal magnet actuating mechanism. A magnet actuating mechanism such as a magnet moving apparatus is disposed outside the liquid storage apparatus, to move the magnets away or close, so as to apply and remove a magnetic field. A transmission screw is driven to rotate by controlling rotation of a drive motor, to drive the magnet frame to move back and forth along the direction of the linear guide rail, to control application and removal of the magnetic field.

The magnets include horizontal magnets and vertical magnets, and the magnets may be formed by strong magnets to rapidly adsorb magnetic particles or magnetic beads. For example, in an implementation, the magnets may be formed by N52 magnets with a relatively strong magnetic force currently available on the market, and the magnetic field strength may be greater than 5000 Gs. The magnets may be arranged in such a manner that the same polarity is in the same plane, so that a direction of the magnetic field is ensured to be vertical to a binding surface of the container. The magnets may be fixed to a movable magnet actuating mechanism, to implement position control of the magnets relative to the liquid storage tank. Preferably, the horizontal magnets may be distributed in a shape completely fitting the outer wall of the liquid storage tank. The magnets may be spread over the entire accessible area of the tank, and an appropriate gap is reserved.

According to an implementation of the present invention, the magnets are horizontal magnets that are movable in a horizontal direction relative to the liquid storage apparatus. According to another implementation of the present invention, the magnets are vertical magnets that are movable in a vertical direction relative to the liquid storage apparatus. According to yet another implementation of the present invention, the magnets include horizontal magnets and vertical magnets, the horizontal magnets are movable in a horizontal direction relative to the liquid storage apparatus, and the vertical magnets are movable in a vertical direction relative to the liquid storage apparatus.

To achieve effective magnetic adsorption and release, the magnets may be moved horizontally, vertically, or both vertically and horizontally to control the movement of the magnets to move close to and away from the liquid storage tank. For example, the vertical magnets (for example, magnetic bars) shown in FIG. 3 may be moved vertically into the liquid storage apparatus to adsorb magnetic beads near the magnetic bars; and the horizontal magnets arranged as shown in FIG. 1 may be moved horizontally to adsorb magnetic beads near the magnets. The vertical magnets entering the liquid storage apparatus may adsorb magnetic beads across the disposable bag.

In some embodiments, the magnet actuating mechanism adopts a symmetrical working mode of pulling ball screws towards two sides. Compared with other transmission modes, the ball screw has the advantages of low noise, small vibration amplitude, and a long service life. The application of the ball screw in the system may promote stability of the magnetic beads after being adsorbed by the magnets and can reduce a loss rate of the magnetic beads in liquid discharging after the adsorption.

Figure 4:
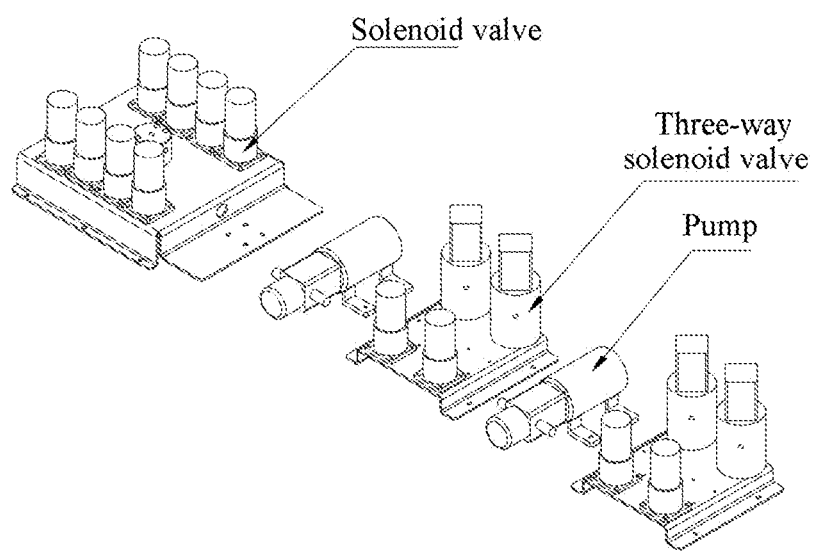
FIG. 4 shows some of solenoid valves, pumps, and pipelines in a magnetic purification system according to an exemplary embodiment of the present invention.

FIG. 4 shows some of solenoid valves, pumps and pipelines in the liquid path system.

The pipeline of the liquid path system is made of a non-sticky material for magnetic beads, to reduce loss of the magnetic beads. For example, an 8-hole valve may be used during switching between pipelines, to reduce the risk of mutual pollution between reagents. A liquid charging pump is driven by a pulse-controlled motor, and may accurately inject or discharge a desired volume. The control system is configured to connect electric parts of the pumps and the solenoid valves in the liquid path system and is responsible for driving the action of the pumps and the valves. The control system may also control the magnet actuating mechanism.

In the control system, all the actuating mechanisms may be automatically controlled by a program, so that manual intervention is reduced, and process data enters the system through AD acquisition, thereby ensuring real-time recording and storage of the data. The speed of the pump may be optimized in the control process. The use of closed-loop control may improve the precision of liquid charging and discharging of the system, and also make the pH value adjustment of the reagent more accurate and rapid. With an integrated human-machine interface, parameters frequently used by a user may be loaded, thereby improving the production efficiency.

An exemplary operation of the large-scale magnetic purification system according to the present invention is as follows.

1. Pumping in magnetic beads
   a) A mixed liquid with 25% magnetic beads was pumped into a reaction vessel. The magnetic beads were washed by using a balancing buffer solution. After stirring, the magnet actuating mechanism was controlled to move the magnets, so that the magnets were close to the vessel. The magnetic beads were adsorbed completely. The supernatant was removed by using the pipeline. The magnetic beads were washed by using the balancing buffer solution for 2-3 times, and the supernatant was removed.
2. Magnetic bead disinfection
   a) 3 CV of 0.1 M NaOH were pumped into the reaction vessel. After stirring, the magnets were moved to completely adsorb the magnetic beads. The supernatant was removed by using the pipeline. 3 CV of 0.1 M NaOH were added again, soaking for more than 30 min. After stirring, the magnets were moved to completely adsorb the magnetic beads, and the supernatant was removed by using the pipeline.
3. Magnetic bead balancing
   a) 3 to 5 CV of balancing buffer solution were pumped into the reaction vessel. After stirring, the magnets were moved to completely adsorb the magnetic beads. The supernatant was removed by using the pipeline. The magnetic beads were washed by using the balancing buffer solution for 5-3 times, and the supernatant was removed. Washing lasted 2-5 min each time.
4. Incubation of fermentation broth
   a) A cell culture solution was pumped into the reaction vessel, and stirring was performed for 2 h.
5. Washing impurities
   a) 3 to 5 CV of balancing buffer solution were pumped into the reaction vessel. After stirring, the magnets were moved to completely adsorb the magnetic beads. The supernatant was removed by using the pipeline. The magnetic beads were washed by using the balancing buffer solution for 5-3 times, and the supernatant was removed. Washing lasted 2-5 min each time.
6. Elution
   a) 5 CV of elution buffer solution were pumped into the reaction vessel. After stirring, the magnets were moved to completely adsorb the magnetic beads, and the eluent was collected. This process was repeated for 3 times.
7. Magnetic bead disinfection
   a) 3 CV of 0.1 M NaOH were pumped into the reaction vessel. After stirring, the magnets were moved to completely adsorb the magnetic beads, and the supernatant was removed by using the pipeline. 3 CV of 0.1 M NaOH were added again, soaking for more than 30 min. After stirring, the magnets were moved to completely adsorb the magnetic beads, and the supernatant was removed by using the pipeline.
8. Magnetic bead collection
   a) 2 CV of 0.01 M NaOH or 20% ethanol were pumped into the reaction vessel. After stirring, the magnetic bead solution was collected by using the pipeline. 2 CV of 0.01 M NaOH or 20% ethanol were pumped into the reaction vessel again. After stirring, the magnetic bead solution was collected by using the pipeline. The pumped mixed magnetic bead solution was collected and stored at 2-8° C.

An application example of the large-scale magnetic purification system according to the present invention is as follows.

Compared with the traditional resin, the large-scale purification based on the magnetic bead greatly improves the purification efficiency, and saves time and labor.

Using 200 L of fermentation broth an example, the purification method based on the magnetic beads saves the operation and time of tank descending and deep filtration, and also saves the sample loading time of a protein A column. The time is reduced from six days to four days, and a single batch of purification saves five to seven full-time equivalents (FTEs).

| Step | Time for resin purification | FTEs for resin purification | Time for magnetic bead purification | FTEs for magnetic bead purification |
| --- | --- | --- | --- | --- |
| Total amount of initial fermentation broth | Tank descending, about three to five hours | 2-3 FTEs | \ | \ |
| Deep filtration | Buffer solution preparation, membrane bag balancing, treatment, deep filtration, about 1-1.5 days | 3-4 FTEs | \ | \ |
| Protein A chromatography | 1 day | 2-3 FTEs | 1 day | 2-3 FTEs |
| Multi-mode chromatography | 1 day | 2-3 FTEs | 1 day | 2-3 FTEs |
| Ion chromatography | 1 day | 2-3 FTEs | 1 day | 2-3 FTEs |

-continued

| Step | Time for resin purification | FTEs for resin purification | Time for magnetic bead purification | FTEs for magnetic bead purification |
|---|---|---|---|---|
| Original liquid preparation | 1 day | 2-3 FTEs | 1 day | 2-3 FTEs |
| Total | About 6 days | About 13-19 FTEs | About 4 days | About 8-12 FTEs |

It should be noted that the embodiments may all be freely combined as required. The foregoing descriptions are merely exemplary implementations of the present invention. A person of ordinary skill in the art may make several variations and improvements without departing from the principle of the present invention, and the variations and improvements shall fall within the protection scope of the present invention.

What is claimed is:

1. A large-scale magnetic purification system, comprising:
a liquid storage apparatus, capable of being connected to a liquid source and a waste liquid barrel through a liquid path system;
a stirring system mounted above the liquid storage apparatus, wherein a stirring paddle of the stirring system is inserted into the liquid storage apparatus for stirring;
magnets mounted around the liquid storage apparatus, wherein the magnets comprise horizontal magnets and vertical magnets, wherein the horizontal magnets are movable in a horizontal direction relative to the liquid storage apparatus, and the vertical magnets are movable in a vertical direction into the liquid storage apparatus;
a magnet actuating mechanism for manipulating the magnets to move away from or close to the liquid storage apparatus; and
a control system, connected to the liquid path system, the magnet actuating mechanism, and the stirring system and controlling the liquid path system, the magnet actuating mechanism, and the stirring system.

2. The large-scale magnetic purification system according to claim 1, wherein the liquid storage apparatus is a liquid storage tank.

3. The large-scale magnetic purification system according to claim 2, wherein a disposable bag is disposed in the liquid storage tank.

4. The large-scale magnetic purification system according to claim 1, wherein the stirring paddle is provided with spiral propeller blades and comprises two sets of opposite blades mounted on one blade shaft.

5. The large-scale magnetic purification system according to claim 1, wherein the magnet actuating mechanism comprises a horizontal magnet actuating mechanism and a vertical magnet actuating mechanism.

6. The large-scale magnetic purification system according to claim 5, wherein the vertical magnets are operable by the vertical magnet actuating mechanism to enter or exit the liquid storage apparatus.

7. The large-scale magnetic purification system according to claim 1, wherein a rotation speed of the stirring system is automatically controlled by a speed-adjustable motor, to control rotation of blades at different speeds.

8. The large-scale magnetic purification system according to claim 1, wherein a pipeline of the liquid path system is made of a non-sticky material for magnetic beads, to reduce loss of the magnetic beads.

9. A method for purifying a biological sample by using the large-scale magnetic purification system according to claim 1, comprising a step of injecting a biological sample containing a target component and magnetic beads capable of binding the target component into the liquid storage apparatus of the large-scale magnetic purification system to perform a purification treatment.

10. The method according to claim 9, wherein a single injection of the biological sample into the liquid storage apparatus for purification is in a range of 100 mL to 10000 L.

11. The method according to claim 9, wherein a single injection of the biological sample into the liquid storage apparatus for purification is in a range of 1 L to 1000 L.

12. The method according to claim 9, wherein a single injection of the biological sample into the liquid storage apparatus for purification is in a range of 10 L to 500 L.

* * * * *